United States Patent
Cruanes et al.

(10) Patent No.: US 11,734,303 B2
(45) Date of Patent: *Aug. 22, 2023

(54) QUERY PROCESSING DISTRIBUTION

(71) Applicant: Snowflake Inc., Bozeman, MT (US)

(72) Inventors: Thierry Cruanes, San Mateo, CA (US); Benoit Dageville, Foster City, CA (US); Marcin Zukowski, San Mateo, CA (US)

(73) Assignee: Snowflake Inc., Bozeman, MT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/805,632

(22) Filed: Feb. 28, 2020

(65) Prior Publication Data
US 2020/0201880 A1 Jun. 25, 2020

Related U.S. Application Data

(63) Continuation of application No. 14/518,971, filed on Oct. 20, 2014.
(Continued)

(51) Int. Cl.
*G06F 16/27* (2019.01)
*G06F 9/48* (2006.01)
(Continued)

(52) U.S. Cl.
CPC ............. *G06F 16/27* (2019.01); *A61F 5/566* (2013.01); *G06F 9/4881* (2013.01);
(Continued)

(58) Field of Classification Search
CPC ...................................................... G06F 16/27
(Continued)

(56) References Cited

U.S. PATENT DOCUMENTS

| 5,787,466 A | 6/1998 | Berliner |
| 6,453,334 B1 | 9/2002 | Vinson et al. |
(Continued)

FOREIGN PATENT DOCUMENTS

| CN | 101120340 A | 2/2008 |
| CN | 102496060 A | 6/2012 |
(Continued)

OTHER PUBLICATIONS

Chen, Weiwei, and Ewa Deelman. "Integration of workflow partitioning and resource provisioning." 2012 12th IEEE/ACM International Symposium on Cluster, Cloud and Grid Computing (ccgrid 2012). IEEE, 2012. (Year: 2012).*
(Continued)

*Primary Examiner* — Mohsen Almani
(74) *Attorney, Agent, or Firm* — Womble Bond Dickinson (US) LLP

(57) ABSTRACT

Example caching systems and methods are described. In one implementation, a method identifies multiple files used to process a query and distributes each of the multiple files to a particular execution node to execute the query. Each execution node determines whether the distributed file is stored in the execution node's cache. If the execution node determines that the file is stored in the cache, it processes the query using the cached file. If the file is not stored in the cache, the execution node retrieves the file from a remote storage device, stores the file in the execution node's cache, and processes the query using the file.

30 Claims, 9 Drawing Sheets

Related U.S. Application Data

(60) Provisional application No. 61/941,986, filed on Feb. 19, 2014.

(51) Int. Cl.

| | | |
|---|---|---|
| *G06F 9/50* | (2006.01) | |
| *G06F 16/14* | (2019.01) | |
| *G06F 16/182* | (2019.01) | |
| *G06F 16/22* | (2019.01) | |
| *G06F 16/21* | (2019.01) | |
| *G06F 16/23* | (2019.01) | |
| *G06F 16/2453* | (2019.01) | |
| *G06F 16/2455* | (2019.01) | |
| *G06F 16/2458* | (2019.01) | |
| *G06F 16/25* | (2019.01) | |
| *G06F 16/28* | (2019.01) | |
| *G06F 16/951* | (2019.01) | |
| *G06F 16/9535* | (2019.01) | |
| *G06F 16/11* | (2019.01) | |
| *H04L 67/1095* | (2022.01) | |
| *H04L 67/1097* | (2022.01) | |
| *H04L 67/568* | (2022.01) | |
| *A61F 5/56* | (2006.01) | |

(52) U.S. Cl.
CPC ......... *G06F 9/5016* (2013.01); *G06F 9/5044* (2013.01); *G06F 9/5083* (2013.01); *G06F 9/5088* (2013.01); *G06F 16/148* (2019.01); *G06F 16/1827* (2019.01); *G06F 16/211* (2019.01); *G06F 16/221* (2019.01); *G06F 16/2365* (2019.01); *G06F 16/2456* (2019.01); *G06F 16/2471* (2019.01); *G06F 16/24532* (2019.01); *G06F 16/24545* (2019.01); *G06F 16/24552* (2019.01); *G06F 16/254* (2019.01); *G06F 16/283* (2019.01); *G06F 16/951* (2019.01); *G06F 16/9535* (2019.01); *H04L 67/1095* (2013.01); *H04L 67/1097* (2013.01); *H04L 67/568* (2022.05)

(58) Field of Classification Search
USPC ....................................................... 707/770
See application file for complete search history.

(56) References Cited

U.S. PATENT DOCUMENTS

| | | | |
|---|---|---|---|
| 6,490,590 | B1 | 12/2002 | Fink |
| 6,757,689 | B2 | 6/2004 | Battas |
| 6,760,765 | B1 | 7/2004 | Asai et al. |
| 7,085,891 | B2 | 8/2006 | Trevathan |
| 7,254,636 | B1 | 8/2007 | O'Toole, Jr. |
| 7,280,998 | B1 | 10/2007 | Aboujaoude |
| 7,823,009 | B1 | 10/2010 | Tormasov |
| 8,341,363 | B2 | 12/2012 | Chou |
| 8,381,015 | B2 | 2/2013 | Kaminski |
| 8,428,087 | B1 | 4/2013 | Vincent |
| 8,516,159 | B2 | 8/2013 | Anathanarayanan |
| 8,516,355 | B2 | 8/2013 | Gale |
| 8,560,887 | B2 | 10/2013 | Behrendt |
| 8,631,131 | B2 * | 1/2014 | Kenneth ............. G06F 9/45558 709/226 |
| 8,640,137 | B1 | 1/2014 | Bostic et al. |
| 8,706,914 | B2 | 4/2014 | Duchesneau |
| 8,725,875 | B2 | 5/2014 | Supalov |
| 9,110,947 | B1 * | 8/2015 | Watzke ................ G06F 16/221 |
| 2002/0120630 | A1 | 8/2002 | Christianson et al. |
| 2002/0147888 | A1 | 10/2002 | Trevathan |
| 2002/0152318 | A1 | 10/2002 | Menon |
| 2003/0158884 | A1 | 8/2003 | Alford, Jr. |
| 2003/0177239 | A1 | 9/2003 | Shinohara et al. |
| 2004/0167904 | A1 | 8/2004 | Wen et al. |
| 2005/0187977 | A1 | 8/2005 | Frost |
| 2005/0198303 | A1 * | 9/2005 | Knauerhase ........ G06F 9/5055 709/227 |
| 2005/0210049 | A1 | 9/2005 | Foster |
| 2006/0059173 | A1 | 3/2006 | Hirsch et al. |
| 2006/0074872 | A1 | 4/2006 | Gordon |
| 2007/0038595 | A1 | 2/2007 | Ghosh et al. |
| 2007/0198656 | A1 | 8/2007 | Mazzaferri et al. |
| 2007/0276861 | A1 | 11/2007 | Pryce et al. |
| 2008/0027788 | A1 | 1/2008 | Lawrence et al. |
| 2008/0027965 | A1 | 1/2008 | Garrett et al. |
| 2008/0104608 | A1 * | 5/2008 | Hyser .................. G06F 9/5088 718/105 |
| 2009/0019103 | A1 | 1/2009 | Tommaney et al. |
| 2009/0150511 | A1 | 6/2009 | Gross et al. |
| 2009/0182836 | A1 | 7/2009 | Aviles et al. |
| 2009/0254516 | A1 | 10/2009 | Meiyyappan et al. |
| 2009/0254532 | A1 | 10/2009 | Yang et al. |
| 2009/0300043 | A1 | 12/2009 | Maclennan |
| 2010/0005054 | A1 | 1/2010 | Smith et al. |
| 2010/0031267 | A1 | 2/2010 | Maessen et al. |
| 2010/0100888 | A1 | 4/2010 | Tene et al. |
| 2010/0145929 | A1 | 6/2010 | Burger |
| 2010/0179940 | A1 | 7/2010 | Gilder et al. |
| 2010/0199042 | A1 | 8/2010 | Bates |
| 2011/0145307 | A1 | 6/2011 | Ananthanarayanan et al. |
| 2011/0161488 | A1 | 6/2011 | Anderson et al. |
| 2011/0225167 | A1 | 9/2011 | Bhattacharjee et al. |
| 2012/0005307 | A1 | 1/2012 | Das et al. |
| 2012/0101860 | A1 | 4/2012 | Ezzat |
| 2012/0109888 | A1 | 5/2012 | Zhang et al. |
| 2012/0110570 | A1 | 5/2012 | Jacobson |
| 2012/0166771 | A1 | 6/2012 | Ringseth |
| 2012/0173824 | A1 | 7/2012 | Iyigun et al. |
| 2012/0204187 | A1 | 8/2012 | Breiter et al. |
| 2012/0233315 | A1 | 9/2012 | Hoffman |
| 2012/0260050 | A1 | 10/2012 | Kaliannan |
| 2012/0265881 | A1 | 10/2012 | Chen |
| 2012/0296883 | A1 | 11/2012 | Ganesh et al. |
| 2012/0311065 | A1 | 12/2012 | Ananthanarayanan et al. |
| 2012/0323971 | A1 | 12/2012 | Pasupuleti |
| 2013/0007753 | A1 | 1/2013 | Jain |
| 2013/0124545 | A1 | 4/2013 | Holmberg et al. |
| 2013/0110778 | A1 | 5/2013 | Taylor et al. |
| 2013/0110961 | A1 | 5/2013 | Jadhav |
| 2013/0132967 | A1 * | 5/2013 | Soundararajan ........ H04L 67/06 718/104 |
| 2013/0145375 | A1 | 6/2013 | Kang |
| 2013/0151884 | A1 | 6/2013 | Hsu |
| 2013/0174146 | A1 | 7/2013 | Dasgupta |
| 2013/0205028 | A1 | 8/2013 | Crockett et al. |
| 2013/0205092 | A1 | 8/2013 | Roy et al. |
| 2013/0218837 | A1 | 8/2013 | Bhatnagar |
| 2013/0282795 | A1 | 10/2013 | Tsao |
| 2013/0332614 | A1 | 12/2013 | Brunk |
| 2014/0025638 | A1 | 1/2014 | Hu |
| 2014/0059226 | A1 | 2/2014 | Messerli |
| 2014/0095646 | A1 | 4/2014 | Chan |
| 2014/0109095 | A1 | 4/2014 | Farkash |
| 2014/0115091 | A1 | 4/2014 | Lee |
| 2014/0136473 | A1 | 5/2014 | Faerber |
| 2014/0149461 | A1 | 5/2014 | Wijayaratne |
| 2014/0229422 | A1 * | 8/2014 | Jain .................... G06F 16/972 707/600 |
| 2014/0258483 | A1 * | 9/2014 | Mai ................... G06F 11/3452 709/223 |

FOREIGN PATENT DOCUMENTS

| | | |
|---|---|---|
| CN | 203261358 U | 10/2013 |
| JP | 2002132455 A | 5/2002 |
| JP | 2005056077 A | 3/2005 |
| JP | 2005-285058 A | 10/2005 |
| JP | 2013156765 A | 8/2013 |
| WO | 2006026659 A2 | 3/2006 |
| WO | 2012158654 A2 | 11/2012 |

(56) References Cited

FOREIGN PATENT DOCUMENTS

| WO | 2013006157 A1 | 1/2013 |
|---|---|---|
| WO | 2013072232 A1 | 5/2013 |
| WO | 2013084078 A1 | 6/2013 |

OTHER PUBLICATIONS

Feng Li et al.: "Distributed data management using MapReduce", ACM Computing Surveys, ACM, New York, NY, US, vol. 46, No. 3, pp. 1-42 (Jan. 1, 2014).
Anonymous: "Cache (computing) Wikipedia", Wikipedia, May 26, 2012.
Anonymous: "NTFS—Wikipedia", Oct. 21, 2013, pp. 1-19.
Azza Abouzeid et al., "HadoopDB", Proceedings of the VLDB Endowment, ACM Digital Library, Assoc. Of Computing Machinery, New York, NY, vol. 2, No. 1 (Aug. 2009).
PCT International Search Report for counterpart PCT Application No. PCT/US2015/016410, 2 pgs. (dated May 21, 2015).
PCT Written Opinion for counterpart PCT Application No. PCT/US2015/016410, 6 pgs. (dated May 21, 2015).
PCT International Preliminary Report on Patentability for PCT Application No. PCT/US2015/016410, 7 pgs. (dated Aug. 23, 2016).
First Examination Report for counterpart Australian Patent Application No. 2015219106, 3 pgs. (dated Jun. 27, 2019).
First Office Action for counterpart Chinese Patent Application No. 201580020415.8, 8 pgs. (dated Oct. 18, 2018).
Second Office Action for counterpart Chinese Patent Application No. 201580020415.8 with English translation, 7 pgs. (dated May 27, 2019).
Extended European Search Report for counterpart Europe Patent Application No. 15752840.7, 11 pgs. (dated Jul. 10, 2017).
Notice of Rejection Ground for counterpart Japanese Patent Application No. 2016-552990, 10 pgs. (dated Jan. 22, 2019).
Notice of Rejection Ground for counterpart Japanese Patent Application No. 2016-552990, 10 pgs. (dated Oct. 1, 2019).
First Office Action for counterpart EP Patent Application No. 15752840.7, 6 pgs. (dated Nov. 5, 2019).

* cited by examiner

QUERY PROCESSING DISTRIBUTION

CROSS REFERENCE TO RELATED APPLICATIONS

This application is a continuation of U.S. patent application Ser. No. 14/518,971, filed Oct. 20, 2014, entitled "Caching Systems and Methods," which claims the benefit of U.S. Provisional Application Ser. No. 61/941,986, entitled "Apparatus and method for enterprise data warehouse data processing on cloud infrastructure," filed Feb. 19, 2014, the disclosure of which is incorporated herein by reference in its entirety.

TECHNICAL FIELD

The present disclosure relates to resource management systems and methods that manage the caching of data.

BACKGROUND

Many existing data storage and retrieval systems are available today. For example, in a shared-disk system, all data is stored on a shared storage device that is accessible from all of the processing nodes in a data cluster. In this type of system, all data changes are written to the shared storage device to ensure that all processing nodes in the data cluster access a consistent version of the data. As the number of processing nodes increases in a shared-disk system, the shared storage device (and the communication links between the processing nodes and the shared storage device) becomes a bottleneck that slows data read and data write operations. This bottleneck is further aggravated with the addition of more processing nodes. Thus, existing shared-disk systems have limited scalability due to this bottleneck problem.

Another existing data storage and retrieval system is referred to as a "shared-nothing architecture." In this architecture, data is distributed across multiple processing nodes such that each node stores a subset of the data in the entire database. When a new processing node is added or removed, the shared-nothing architecture must rearrange data across the multiple processing nodes. This rearrangement of data can be time-consuming and disruptive to data read and write operations executed during the data rearrangement. And, the affinity of data to a particular node can create "hot spots" on the data cluster for popular data. Further, since each processing node performs also the storage function, this architecture requires at least one processing node to store data. Thus, the shared-nothing architecture fails to store data if all processing nodes are removed. Additionally, management of data in a shared-nothing architecture is complex due to the distribution of data across many different processing nodes.

The systems and methods described herein provide an improved approach to data storage and data retrieval that alleviates the above-identified limitations of existing systems.

BRIEF DESCRIPTION OF THE DRAWINGS

Non-limiting and non-exhaustive embodiments of the present disclosure are described with reference to the following figures, wherein like reference numerals refer to like parts throughout the various figures unless otherwise specified.

DETAILED DESCRIPTION

Figure 1:
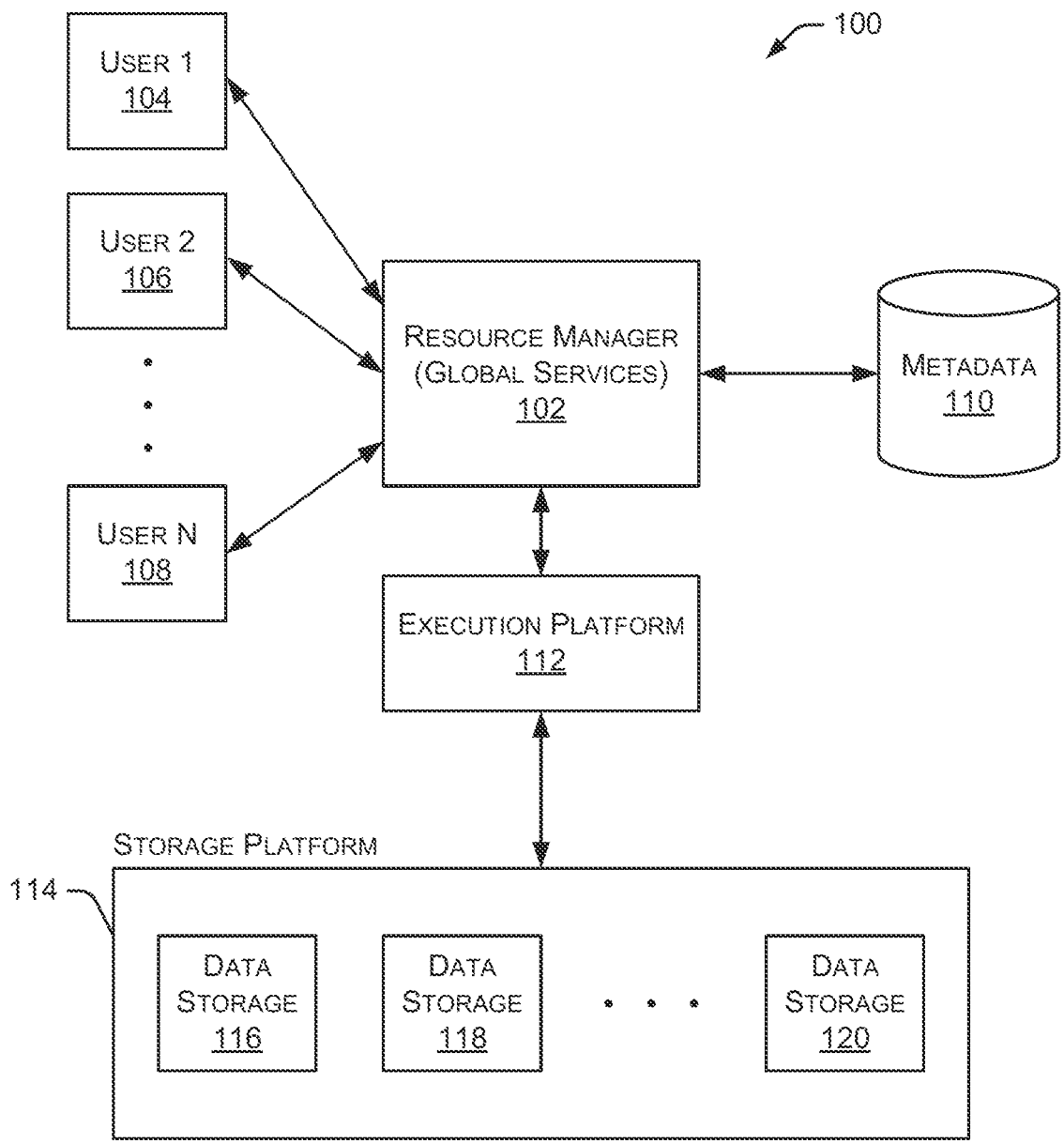
FIG. 1 is a block diagram depicting an example embodiment of the systems and methods described herein.

The systems and methods described herein provide a new platform for storing and retrieving data without the problems faced by existing systems. For example, this new platform supports the addition of new nodes without the need for rearranging data files as required by the shared-nothing architecture. Additionally, nodes can be added to the platform without creating bottlenecks that are common in the shared-disk system. This new platform is always available for data read and data write operations, even when some of the nodes are offline for maintenance or have suffered a failure. The described platform separates the data storage resources from the computing resources so that data can be stored without requiring the use of dedicated computing resources. This is an improvement over the shared-nothing architecture, which fails to store data if all computing resources are removed. Therefore, the new platform continues to store data even though the computing resources are no longer available or are performing other tasks.

In the following description, reference is made to the accompanying drawings that form a part thereof, and in which is shown by way of illustration specific exemplary embodiments in which the disclosure may be practiced. These embodiments are described in sufficient detail to enable those skilled in the art to practice the concepts disclosed herein, and it is to be understood that modifications to the various disclosed embodiments may be made, and other embodiments may be utilized, without departing from the scope of the present disclosure. The following detailed description is, therefore, not to be taken in a limiting sense.

Reference throughout this specification to "one embodiment," "an embodiment," "one example" or "an example" means that a particular feature, structure or characteristic described in connection with the embodiment or example is included in at least one embodiment of the present disclosure. Thus, appearances of the phrases "in one embodiment," "in an embodiment," "one example" or "an example" in various places throughout this specification are not necessarily all referring to the same embodiment or example. In addition, it should be appreciated that the figures provided herewith are for explanation purposes to persons ordinarily skilled in the art and that the drawings are not necessarily drawn to scale.

Embodiments in accordance with the present disclosure may be embodied as an apparatus, method or computer program product. Accordingly, the present disclosure may take the form of an entirely hardware-comprised embodiment, an entirely software-comprised embodiment (including firmware, resident software, micro-code, etc.) or an embodiment combining software and hardware aspects that may all generally be referred to herein as a "circuit," "module" or "system." Furthermore, embodiments of the present disclosure may take the form of a computer program product embodied in any tangible medium of expression having computer-usable program code embodied in the medium.

Any combination of one or more computer-usable or computer-readable media may be utilized. For example, a computer-readable medium may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present disclosure may be written in any combination of one or more programming languages. Such code may be compiled from source code to computer-readable assembly language or machine code suitable for the device or computer on which the code will be executed.

Embodiments may also be implemented in cloud computing environments. In this description and the following claims, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction and then scaled accordingly. A cloud model can be composed of various characteristics (e.g., on-demand self-service, broad network access, resource pooling, rapid elasticity, and measured service), service models (e.g., Software as a Service ("SaaS"), Platform as a Service ("PaaS"), and Infrastructure as a Service ("IaaS")), and deployment models (e.g., private cloud, community cloud, public cloud, and hybrid cloud).

The flow diagrams and block diagrams in the attached figures illustrate the architecture, functionality, and operation of possible implementations of systems, methods, and computer program products according to various embodiments of the present disclosure. In this regard, each block in the flow diagrams or block diagrams may represent a module, segment, or portion of code, which comprises one or more executable instructions for implementing the specified logical function(s). It will also be noted that each block of the block diagrams and/or flow diagrams, and combinations of blocks in the block diagrams and/or flow diagrams, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flow diagram and/or block diagram block or blocks.

The systems and methods described herein provide a flexible and scalable data warehouse using a new data processing platform. In some embodiments, the described systems and methods leverage a cloud infrastructure that supports cloud-based storage resources, computing resources, and the like. Example cloud-based storage resources offer significant storage capacity available on-demand at a low cost. Further, these cloud-based storage resources may be fault-tolerant and highly scalable, which can be costly to achieve in private data storage systems. Example cloud-based computing resources are available on-demand and may be priced based on actual usage levels of the resources. Typically, the cloud infrastructure is dynamically deployed, reconfigured, and decommissioned in a rapid manner.

In the described systems and methods, a data storage system utilizes an SQL (Structured Query Language)-based relational database. However, these systems and methods are applicable to any type of database, and any type of data storage and retrieval platform, using any data storage architecture and using any language to store and retrieve data within the data storage and retrieval platform. The systems and methods described herein further provide a multi-tenant system that supports isolation of computing resources and data between different customers/clients and between different users within the same customer/client.

FIG. 1 is a block diagram depicting an example embodiment of a new data processing platform 100. As shown in FIG. 1, a resource manager 102 is coupled to multiple users 104, 106, and 108. In particular implementations, resource manager 102 can support any number of users desiring access to data processing platform 100. Users 104-108 may include, for example, end users providing data storage and retrieval requests, system administrators managing the systems and methods described herein, and other components/devices that interact with resource manager 102. Resource manager 102 provides various services and functions that support the operation of all systems and components within data processing platform 100. As used herein, resource manager 102 may also be referred to as a "global services system" that performs various functions as discussed herein.

Resource manager 102 is also coupled to metadata 110, which is associated with the entirety of data stored throughout data processing platform 100. In some embodiments, metadata 110 includes a summary of data stored in remote data storage systems as well as data available from a local cache. Additionally, metadata 110 may include information regarding how data is organized in the remote data storage systems and the local caches. Metadata 110 allows systems and services to determine whether a piece of data needs to be accessed without loading or accessing the actual data from a storage device.

Resource manager 102 is further coupled to an execution platform 112, which provides multiple computing resources that execute various data storage and data retrieval tasks, as discussed in greater detail below. Execution platform 112 is coupled to multiple data storage devices 116, 118, and 120 that are part of a storage platform 114. Although three data storage devices 116, 118, and 120 are shown in FIG. 1, execution platform 112 is capable of communicating with any number of data storage devices. In some embodiments, data storage devices 116, 118, and 120 are cloud-based storage devices located in one or more geographic locations. For example, data storage devices 116, 118, and 120 may be part of a public cloud infrastructure or a private cloud infrastructure. Data storage devices 116, 118, and 120 may be hard disk drives (HDDs), solid state drives (SSDs), storage clusters, Amazon S3™ storage systems or any other data storage technology. Additionally, storage platform 114 may include distributed file systems (such as Hadoop Distributed File Systems (HDFS)), object storage systems, and the like.

In particular embodiments, the communication links between resource manager 102 and users 104-108, metadata 110, and execution platform 112 are implemented via one or more data communication networks. Similarly, the communication links between execution platform 112 and data storage devices 116-120 in storage platform 114 are implemented via one or more data communication networks. These data communication networks may utilize any communication protocol and any type of communication medium. In some embodiments, the data communication networks are a combination of two or more data communication networks (or sub-networks) coupled to one another. In alternate embodiments, these communication links are implemented using any type of communication medium and any communication protocol.

As shown in FIG. 1, data storage devices 116, 118, and 120 are decoupled from the computing resources associated with execution platform 112. This architecture supports dynamic changes to data processing platform 100 based on the changing data storage/retrieval needs as well as the changing needs of the users and systems accessing data processing platform 100. The support of dynamic changes allows data processing platform 100 to scale quickly in response to changing demands on the systems and components within data processing platform 100. The decoupling of the computing resources from the data storage devices supports the storage of large amounts of data without requiring a corresponding large amount of computing resources. Similarly, this decoupling of resources supports a significant increase in the computing resources utilized at a particular time without requiring a corresponding increase in the available data storage resources.

Resource manager 102, metadata 110, execution platform 112, and storage platform 114 are shown in FIG. 1 as individual components. However, each of resource manager 102, metadata 110, execution platform 112, and storage platform 114 may be implemented as a distributed system (e.g., distributed across multiple systems/platforms at multiple geographic locations). Additionally, each of resource manager 102, metadata 110, execution platform 112, and storage platform 114 can be scaled up or down (independently of one another) depending on changes to the requests received from users 104-108 and the changing needs of data processing platform 100. Thus, in the described embodiments, data processing platform 100 is dynamic and supports regular changes to meet the current data processing needs.

During typical operation, data processing platform 100 processes multiple queries (or requests) received from any of the users 104-108. These queries are managed by resource manager 102 to determine when and how to execute the queries. For example, resource manager 102 may determine what data is needed to process the query and further determine which nodes within execution platform 112 are best suited to process the query. Some nodes may have already cached the data needed to process the query and, therefore, are good candidates for processing the query. Metadata 110 assists resource manager 102 in determining which nodes in execution platform 112 already cache at least a portion of the data needed to process the query. One or more nodes in execution platform 112 process the query using data cached by the nodes and, if necessary, data retrieved from storage platform 114. It is desirable to retrieve as much data as possible from caches within execution platform 112 because the retrieval speed is typically much faster than retrieving data from storage platform 114.

As shown in FIG. 1, data processing platform 100 separates execution platform 112 from storage platform 114. In this arrangement, the processing resources and cache resources in execution platform 112 operate independently of the data storage resources 116-120 in storage platform 114. Thus, the computing resources and cache resources are not restricted to specific data storage resources 116-120. Instead, all computing resources and all cache resources may retrieve data from, and store data to, any of the data storage resources in storage platform 114. Additionally, data processing platform 100 supports the addition of new computing resources and cache resources to execution platform 112 without requiring any changes to storage platform 114. Similarly, data processing platform 100 supports the addition of data storage resources to storage platform 114 without requiring any changes to nodes in execution platform 112.

Figure 2:
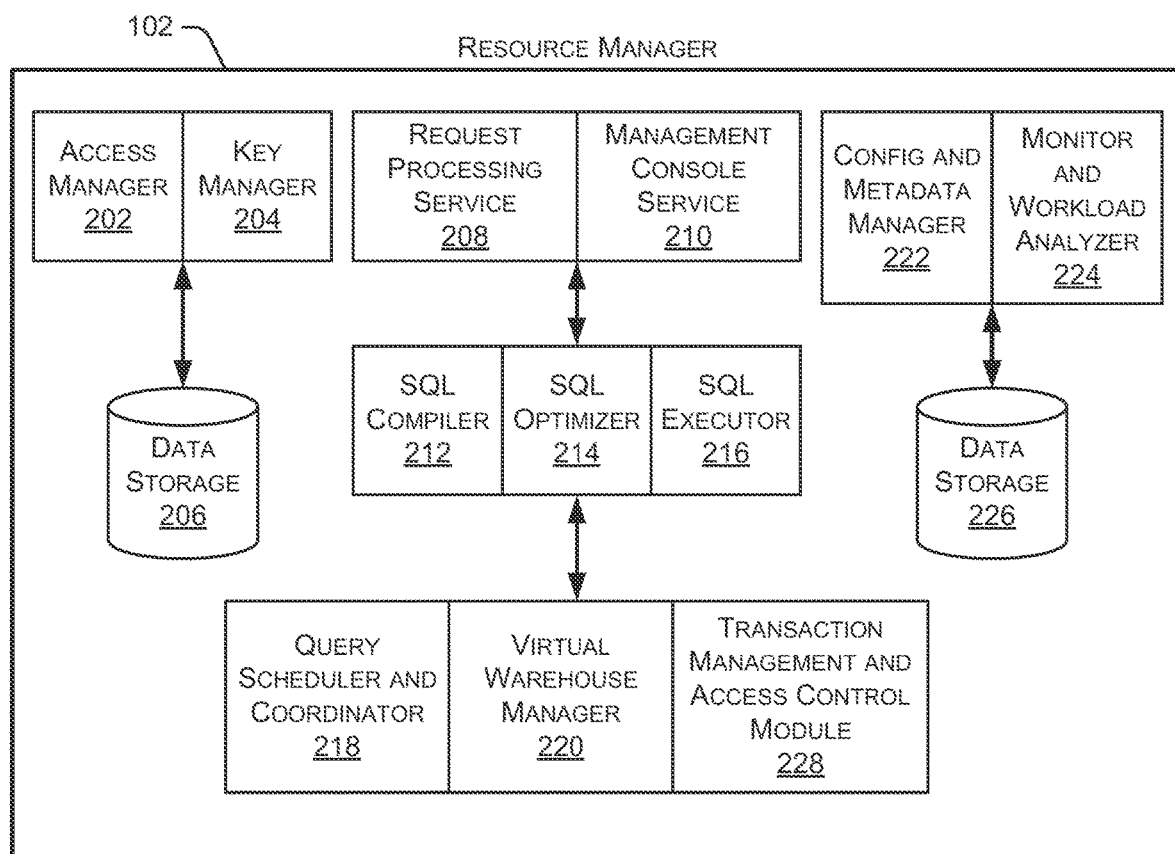
FIG. 2 is a block diagram depicting an embodiment of a resource manager.

FIG. 2 is a block diagram depicting an embodiment of resource manager 102. As shown in FIG. 2, resource manager 102 includes an access manager 202 and a key manager 204 coupled to a data storage device 206. Access manager 202 handles authentication and authorization tasks for the systems described herein. Key manager 204 manages storage and authentication of keys used during authentication and authorization tasks. For example, access manager 202 and key manager 204 manage the keys used to access data stored in remote storage devices (e.g., data storage devices in storage platform 114). As used herein, the remote storage devices may also be referred to as "persistent storage devices." A request processing service 208 manages received data storage requests and data retrieval requests (e.g., database queries). For example, request processing service 208 may determine the data necessary to process the received data storage request or data retrieval request. The necessary data may be stored in a cache within execution platform 112 (as discussed in greater detail below) or in a data storage device in storage platform 114. A management console service 210 supports access to various systems and processes by administrators and other system managers. Additionally, management console service 210 may receive requests from users 104-108 to issue queries and monitor the workload on the system. In some embodiments, a particular user may issue a request to monitor the workload that their specific query places on the system.

Resource manager 102 also includes an SQL compiler 212, an SQL optimizer 214 and an SQL executor 210. SQL compiler 212 parses SQL queries and generates the execution code for the queries. SQL optimizer 214 determines the best method to execute queries based on the data that needs to be processed. SQL optimizer 214 also handles various data pruning operations and other data optimization techniques to improve the speed and efficiency of executing the SQL query. SQL executor 216 executes the query code for queries received by resource manager 102.

A query scheduler and coordinator 218 sends received queries to the appropriate services or systems for compilation, optimization, and dispatch to execution platform 112. For example, queries may be prioritized and processed in that prioritized order. In some embodiments, query scheduler and coordinator 218 identifies or assigns particular nodes in execution platform 112 to process particular queries. A virtual warehouse manager 220 manages the operation of multiple virtual warehouses implemented in execution platform 112. As discussed below, each virtual warehouse includes multiple execution nodes that each include a cache and a processor.

Additionally, resource manager 102 includes a configuration and metadata manager 222, which manages the information related to the data stored in the remote data storage devices and in the local caches (i.e., the caches in execution platform 112). As discussed in greater detail below, configuration and metadata manager 222 uses the metadata to determine which data files need to be accessed to retrieve data for processing a particular query. A monitor and workload analyzer 224 oversees the processes performed by resource manager 102 and manages the distribution of tasks (e.g., workload) across the virtual warehouses and execution nodes in execution platform 112. Monitor and workload analyzer 224 also redistributes tasks, as needed, based on changing workloads throughout data processing platform 100. Configuration and metadata manager 222 and monitor and workload analyzer 224 are coupled to a data storage device 226. Data storage devices 206 and 226 in FIG. 2 represent any data storage device within data processing platform 100. For example, data storage devices 206 and 226 may represent caches in execution platform 112, storage devices in storage platform 114, or any other storage device.

Resource manager 102 also includes a transaction management and access control module 228, which manages the various tasks and other activities associated with the processing of data storage requests and data access requests. For example, transaction management and access control module 228 provides consistent and synchronized access to data by multiple users or systems. Since multiple users/systems may access the same data simultaneously, changes to the data must be synchronized to ensure that each user/system is working with the current version of the data. Transaction management and access control module 228 provides control of various data processing activities at a single, centralized location in resource manager 102. In some embodiments, transaction management and access control module 228 interacts with SQL executor 216 to support the management of various tasks being executed by SQL executor 216.

Figure 3:
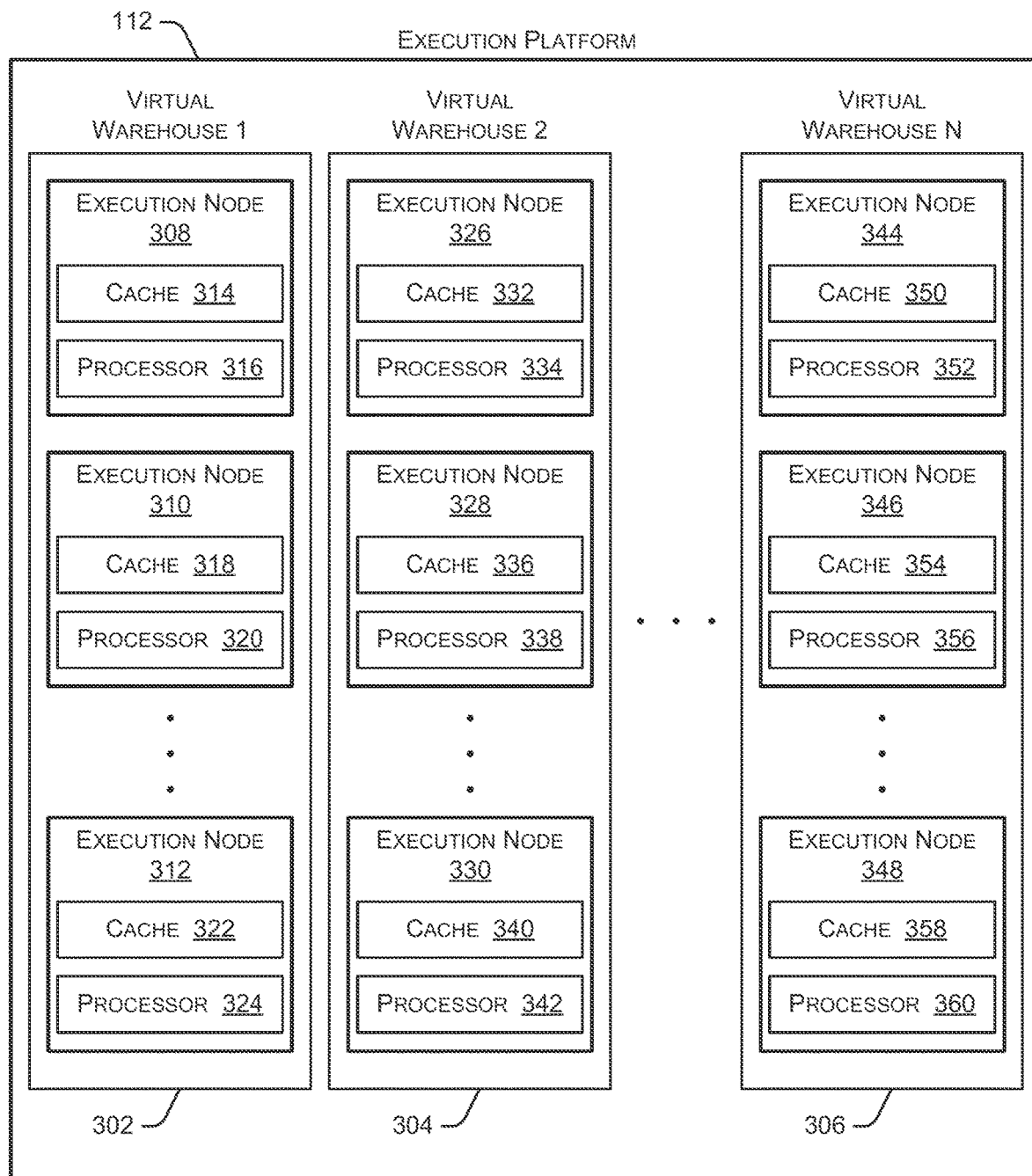
FIG. 3 is a block diagram depicting an embodiment of an execution platform.

FIG. 3 is a block diagram depicting an embodiment of an execution platform 112. As shown in FIG. 3, execution platform 112 includes multiple virtual warehouses 302, 304, and 306. Each virtual warehouse includes multiple execution nodes that each include a data cache and a processor. Virtual warehouses 302, 304, and 306 are capable of executing multiple queries (and other tasks) in parallel by using the multiple execution nodes. As discussed herein, execution platform 112 can add new virtual warehouses and drop existing virtual warehouses in real time based on the current processing needs of the systems and users. This flexibility allows execution platform 112 to quickly deploy large amounts of computing resources when needed without being forced to continue paying for those computing resources when they are no longer needed. All virtual warehouses can access data from any data storage device (e.g., any storage device in storage platform 114).

Although each virtual warehouse 302-306 shown in FIG. 3 includes three execution nodes, a particular virtual warehouse may include any number of execution nodes. Further, the number of execution nodes in a virtual warehouse is dynamic, such that new execution nodes are created when additional demand is present, and existing execution nodes are deleted when they are no longer necessary.

Each virtual warehouse 302-306 is capable of accessing any of the data storage devices 116-120 shown in FIG. 1. Thus, virtual warehouses 302-306 are not necessarily assigned to a specific data storage device 116-120 and, instead, can access data from any of the data storage devices 116-120. Similarly, each of the execution nodes shown in FIG. 3 can access data from any of the data storage devices 116-120. In some embodiments, a particular virtual warehouse or a particular execution node may be temporarily assigned to a specific data storage device, but the virtual warehouse or execution node may later access data from any other data storage device.

In the example of FIG. 3, virtual warehouse 302 includes three execution nodes 308, 310, and 312. Execution node 308 includes a cache 314 and a processor 316. Execution node 310 includes a cache 318 and a processor 320. Execution node 312 includes a cache 322 and a processor 324. Each execution node 308-312 is associated with processing one or more data storage and/or data retrieval tasks. For example, a particular virtual warehouse may handle data storage and data retrieval tasks associated with a particular user or customer. In other implementations, a particular virtual warehouse may handle data storage and data retrieval tasks associated with a particular data storage system or a particular category of data.

Similar to virtual warehouse 302 discussed above, virtual warehouse 304 includes three execution nodes 326, 328, and 330. Execution node 326 includes a cache 332 and a processor 334. Execution node 328 includes a cache 336 and a processor 338. Execution node 330 includes a cache 340 and a processor 342. Additionally, virtual warehouse 306 includes three execution nodes 344, 346, and 348. Execution node 344 includes a cache 350 and a processor 352. Execution node 346 includes a cache 354 and a processor 356. Execution node 348 includes a cache 358 and a processor 360.

In some embodiments, the execution nodes shown in FIG. 3 are stateless with respect to the data the execution nodes are caching. For example, these execution nodes do not store or otherwise maintain state information about the execution node or the data being cached by a particular execution node. Thus, in the event of an execution node failure, the failed node can be transparently replaced by another node. Since there is no state information associated with the failed execution node, the new (replacement) execution node can easily replace the failed node without concern for recreating a particular state.

Although the execution nodes shown in FIG. 3 each include one data cache and one processor, alternate embodiments may include execution nodes containing any number of processors and any number of caches. Additionally, the caches may vary in size among the different execution nodes. The caches shown in FIG. 3 store, in the local execution node, data that was retrieved from one or more data storage devices in storage platform 114 (FIG. 1). Thus, the caches reduce or eliminate the bottleneck problems occurring in platforms that consistently retrieve data from remote storage systems. Instead of repeatedly accessing data from the remote storage devices, the systems and methods described herein access data from the caches in the execution nodes which is significantly faster and avoids the bottleneck problem discussed above. In some embodiments, the caches are implemented using high-speed memory devices that provide fast access to the cached data. Each cache can store data from any of the storage devices in storage platform 114.

Further, the cache resources and computing resources may vary between different execution nodes. For example, one execution node may contain significant computing resources and minimal cache resources, making the execution node useful for tasks that require significant computing resources. Another execution node may contain significant cache resources and minimal computing resources, making this execution node useful for tasks that require caching of large amounts of data. Yet another execution node may contain cache resources providing faster input-output operations, useful for tasks that require fast scanning of large amounts of data. In some embodiments, the cache resources and computing resources associated with a particular execution node are determined when the execution node is created, based on the expected tasks to be performed by the execution node.

Additionally, the cache resources and computing resources associated with a particular execution node may change over time based on changing tasks performed by the execution node. For example, a particular execution node may be assigned more processing resources if the tasks performed by the execution node become more processor intensive. Similarly, an execution node may be assigned more cache resources if the tasks performed by the execution node require a larger cache capacity.

Although virtual warehouses 302-306 are associated with the same execution platform 112, the virtual warehouses may be implemented using multiple computing systems at multiple geographic locations. For example, virtual warehouse 302 can be implemented by a computing system at a first geographic location, while virtual warehouses 304 and 306 are implemented by another computing system at a second geographic location. In some embodiments, these different computing systems are cloud-based computing systems maintained by one or more different entities.

Additionally, each virtual warehouse is shown in FIG. 3 as having multiple execution nodes. The multiple execution nodes associated with each virtual warehouse may be implemented using multiple computing systems at multiple geographic locations. For example, a particular instance of virtual warehouse 302 implements execution nodes 308 and 310 on one computing platform at a particular geographic location, and implements execution node 312 at a different computing platform at another geographic location. Selecting particular computing systems to implement an execution node may depend on various factors, such as the level of resources needed for a particular execution node (e.g., processing resource requirements and cache requirements), the resources available at particular computing systems, communication capabilities of networks within a geographic location or between geographic locations, and which computing systems are already implementing other execution nodes in the virtual warehouse.

Execution platform 112 is also fault tolerant. For example, if one virtual warehouse fails, that virtual warehouse is quickly replaced with a different virtual warehouse at a different geographic location.

A particular execution platform 112 may include any number of virtual warehouses 302-306. Additionally, the number of virtual warehouses in a particular execution platform is dynamic, such that new virtual warehouses are created when additional processing and/or caching resources are needed. Similarly, existing virtual warehouses may be deleted when the resources associated with the virtual warehouse are no longer necessary.

In some embodiments, virtual warehouses 302, 304, and 306 may operate on the same data in storage platform 114, but each virtual warehouse has its own execution nodes with independent processing and caching resources. This configuration allows requests on different virtual warehouses to be processed independently and with no interference between the requests. This independent processing, combined with the ability to dynamically add and remove virtual warehouses, supports the addition of new processing capacity for new users without impacting the performance observed by the existing users.

Figure 4:
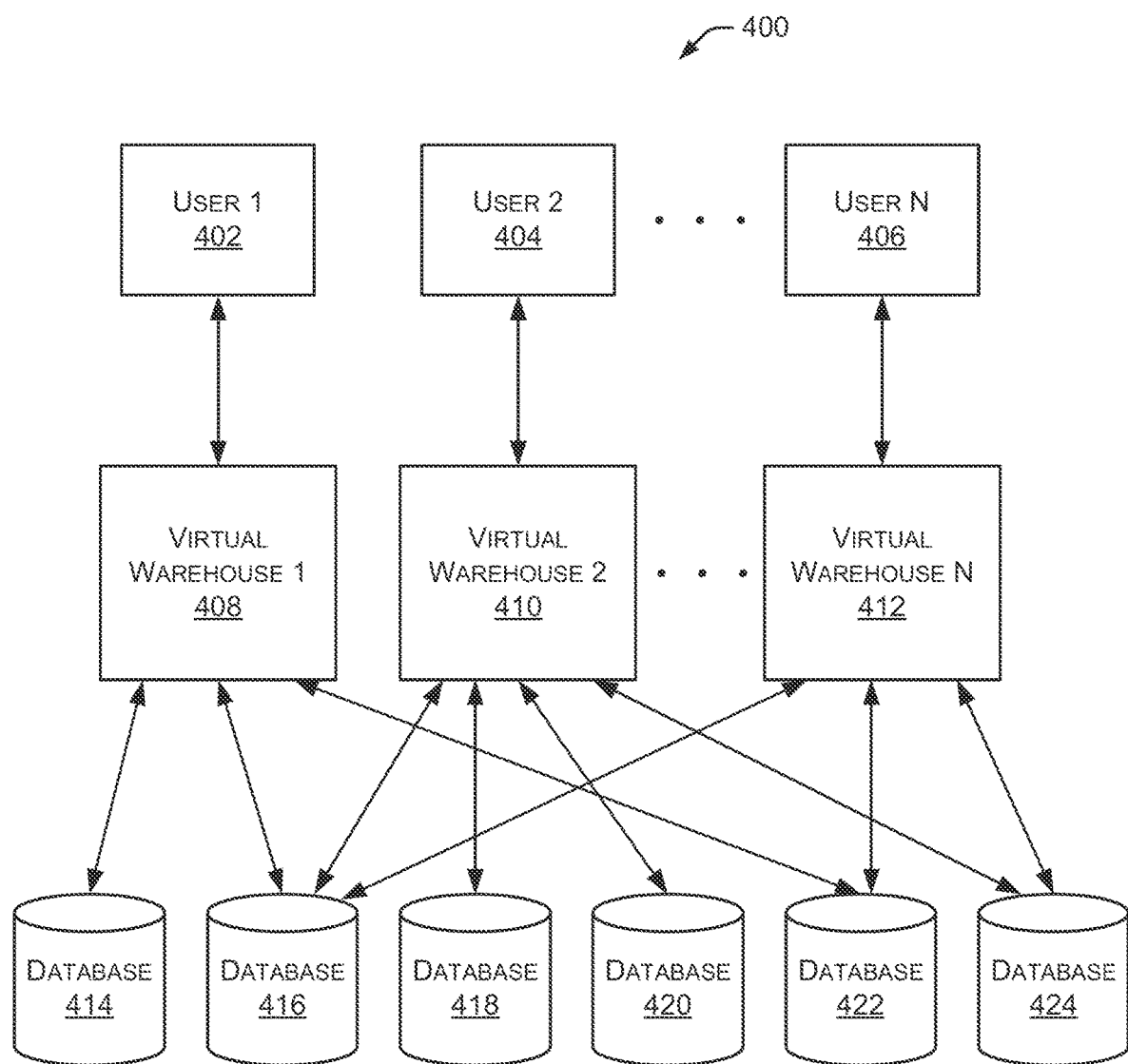
FIG. 4 is a block diagram depicting an example operating environment with multiple users accessing multiple databases through multiple virtual warehouses.

FIG. 4 is a block diagram depicting an example operating environment 400 with multiple users accessing multiple databases through multiple virtual warehouses. In environment 400, multiple users 402, 404, and 406 access multiple databases 414, 416, 418, 420, 422, and 424 through multiple virtual warehouses 408, 410, and 412. Although not shown in FIG. 4, users 402, 404, and 406 may access virtual warehouses 408, 410, and 412 through resource manager 102 (FIG. 1). In particular embodiments, databases 414-424 are contained in storage platform 114 (FIG. 1) and are accessible by any virtual warehouse implemented in execution platform 112. In some embodiments, users 402-406 access one of the virtual warehouses 408-412 using a data communication network, such as the Internet. In some implementations, each user 402-406 specifies a particular virtual warehouse 408-412 to work with at a specific time. In the example of FIG. 4, user 402 interacts with virtual warehouse 408, user 404 interacts with virtual warehouse 410, and user 406 interacts with virtual warehouse 412. Thus, user 402 submits data retrieval and data storage requests through virtual warehouse 408. Similarly, users 404 and 406 submit data retrieval and data storage requests through virtual warehouses 410 and 412, respectively.

Each virtual warehouse 408-412 is configured to communicate with a subset of all databases 414-424. For example, in environment 400, virtual warehouse 408 is configured to communicate with databases 414, 416, and 422. Similarly, virtual warehouse 410 is configured to communicate with databases 416, 418, 420, and 424. And, virtual warehouse 412 is configured to communicate with databases 416, 422, and 424. In alternate embodiments, one or more of virtual warehouses 408-412 communicate with all of the databases 414-424. The arrangement shown in FIG. 4 allows individual users to send all data retrieval and data storage requests through a single virtual warehouse. That virtual warehouse processes the data retrieval and data storage tasks using cached data within one of the execution nodes in the virtual warehouse, or retrieves (and caches) the necessary data from an appropriate database. The mappings between the virtual warehouses is a logical mapping, not a hardware mapping. This logical mapping is based on access control parameters related to security and resource access management settings. The logical mappings are easily changed without requiring reconfiguration of the virtual warehouse or storage resources.

Although environment 400 shows virtual warehouses 408-412 configured to communicate with specific subsets of databases 414-424, that configuration is dynamic. For example, virtual warehouse 408 may be reconfigured to communicate with a different subset of databases 414-424 based on changing tasks to be performed by virtual warehouse 408. For instance, if virtual warehouse 408 receives requests to access data from database 418, virtual warehouse 408 may be reconfigured to also communicate with database 418. If, at a later time, virtual warehouse 408 no longer needs to access data from database 418, virtual warehouse 408 may be reconfigured to delete the communication with database 418.

Figure 5:
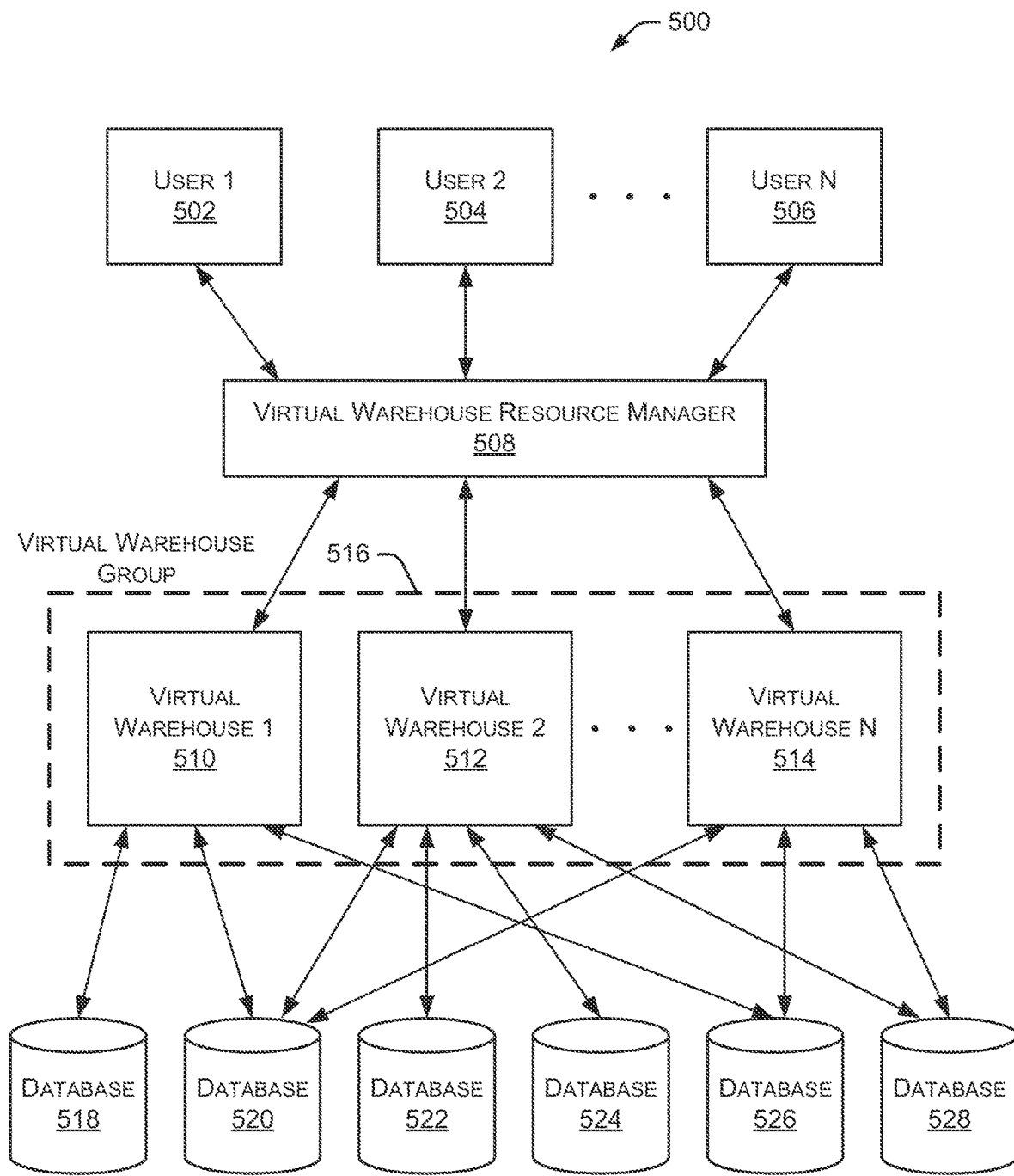
FIG. 5 is a block diagram depicting another example operating environment with multiple users accessing multiple databases through a load balancer and multiple virtual warehouses contained in a virtual warehouse group.

FIG. 5 is a block diagram depicting another example operating environment 500 with multiple users accessing multiple databases through a load balancer and multiple virtual warehouses contained in a virtual warehouse group.

Environment 500 is similar to environment 400 (FIG. 4), but additionally includes a virtual warehouse resource manager 508 and multiple virtual warehouses 510, 512, and 514 arranged in a virtual warehouse group 516. Virtual warehouse resource manager 508 may be contained in resource manager 102. In particular, multiple users 502, 504, and 506 access multiple databases 518, 520, 522, 524, 526, and 528 through virtual warehouse resource manager 508 and virtual warehouse group 516. In some embodiments, users 502-506 access virtual warehouse resource manager 508 using a data communication network, such as the Internet. Although not shown in FIG. 5, users 502, 504, and 506 may access virtual warehouse resource manager 508 through resource manager 102 (FIG. 1). In some embodiments, virtual warehouse resource manager 508 is implemented within resource manager 102.

Users 502-506 may submit data retrieval and data storage requests to virtual warehouse resource manager 508, which routes the data retrieval and data storage requests to an appropriate virtual warehouse 510-514 in virtual warehouse group 516. In some implementations, virtual warehouse resource manager 508 provides a dynamic assignment of users 502-506 to virtual warehouses 510-514. When submitting a data retrieval or data storage request, users 502-506 may specify virtual warehouse group 516 to process the request without specifying the particular virtual warehouse 510-514 that will process the request. This arrangement allows virtual warehouse resource manager 508 to distribute multiple requests across the virtual warehouses 510-514 based on efficiency, available resources, and the availability of cached data within the virtual warehouses 510-514. When determining how to route data processing requests, virtual warehouse resource manager 508 considers available resources, current resource loads, number of current users, and the like.

In some embodiments, fault tolerance systems create a new virtual warehouses in response to a failure of a virtual warehouse. The new virtual warehouse may be in the same virtual warehouse group or may be created in a different virtual warehouse group at a different geographic location.

Each virtual warehouse 510-514 is configured to communicate with a subset of all databases 518-528. For example, in environment 500, virtual warehouse 510 is configured to communicate with databases 518, 520, and 526. Similarly, virtual warehouse 512 is configured to communicate with databases 520, 522, 524, and 528. And, virtual warehouse 514 is configured to communicate with databases 520, 526, and 528. In alternate embodiments, virtual warehouses 510-514 may communicate with any (or all) of the databases 518-528.

Although environment 500 shows one virtual warehouse group 516, alternate embodiments may include any number of virtual warehouse groups, each associated with any number of virtual warehouses. The number of virtual warehouse groups in a particular environment is dynamic and may change based on the changing needs of the users and other systems in the environment.

Figure 6:
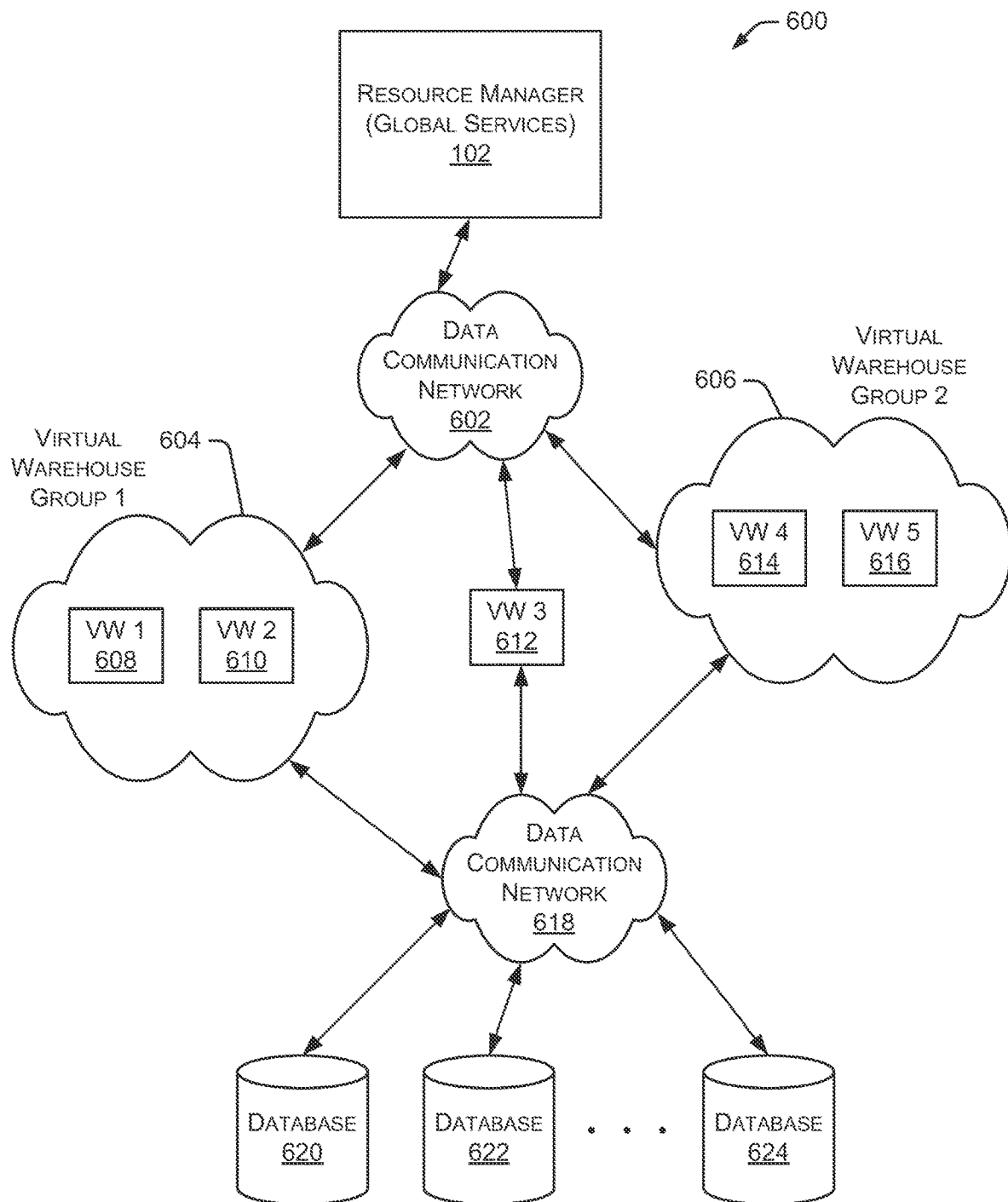
FIG. 6 is a block diagram depicting another example operating environment having multiple distributed virtual warehouses and virtual warehouse groups.

FIG. 6 is a block diagram depicting another example operating environment 600 having multiple distributed virtual warehouses and virtual warehouse groups. Environment 600 includes resource manager 102 that communicates with virtual warehouse groups 604 and 606 through a data communication network 602. Warehouse group 604 includes two virtual warehouses 608 and 610, and warehouse group 606 includes another two virtual warehouses 614 and 616. Resource manager 102 also communicates with virtual warehouse 612 (which is not part of a virtual warehouse group) through data communication network 602.

Virtual warehouse groups 604 and 606 as well as virtual warehouse 612 communicate with databases 620, 622, and 624 through a data communication network 618. In some embodiments data communication networks 602 and 618 are the same network. Environment 600 allows resource manager 102 to coordinate user data storage and retrieval requests across the multiple virtual warehouses 608-616 to store and retrieve data in databases 620-624. Virtual warehouse groups 604 and 606 can be located in the same geographic area, or can be separated geographically. Additionally, virtual warehouse groups 604 and 606 can be implemented by the same entity or by different entities.

The systems and methods described herein allow data to be stored and accessed as a service that is separate from computing (or processing) resources. Even if no computing resources have been allocated from the execution platform, data is available to a virtual warehouse without requiring reloading of the data from a remote data source. Thus, data is available independently of the allocation of computing resources associated with the data. The described systems and methods are useful with any type of data. In particular embodiments, data is stored in a structured, optimized format. The decoupling of the data storage/access service from the computing services also simplifies the sharing of data among different users and groups. As discussed herein, each virtual warehouse can access any data to which it has access permissions, even at the same time as other virtual warehouses are accessing the same data. This architecture supports running queries without any actual data stored in the local cache. The systems and methods described herein are capable of transparent dynamic data movement, which moves data from a remote storage device to a local cache, as needed, in a manner that is transparent to the user of the system. Further, this architecture supports data sharing without prior data movement since any virtual warehouse can access any data due to the decoupling of the data storage service from the computing service.

Figure 7:
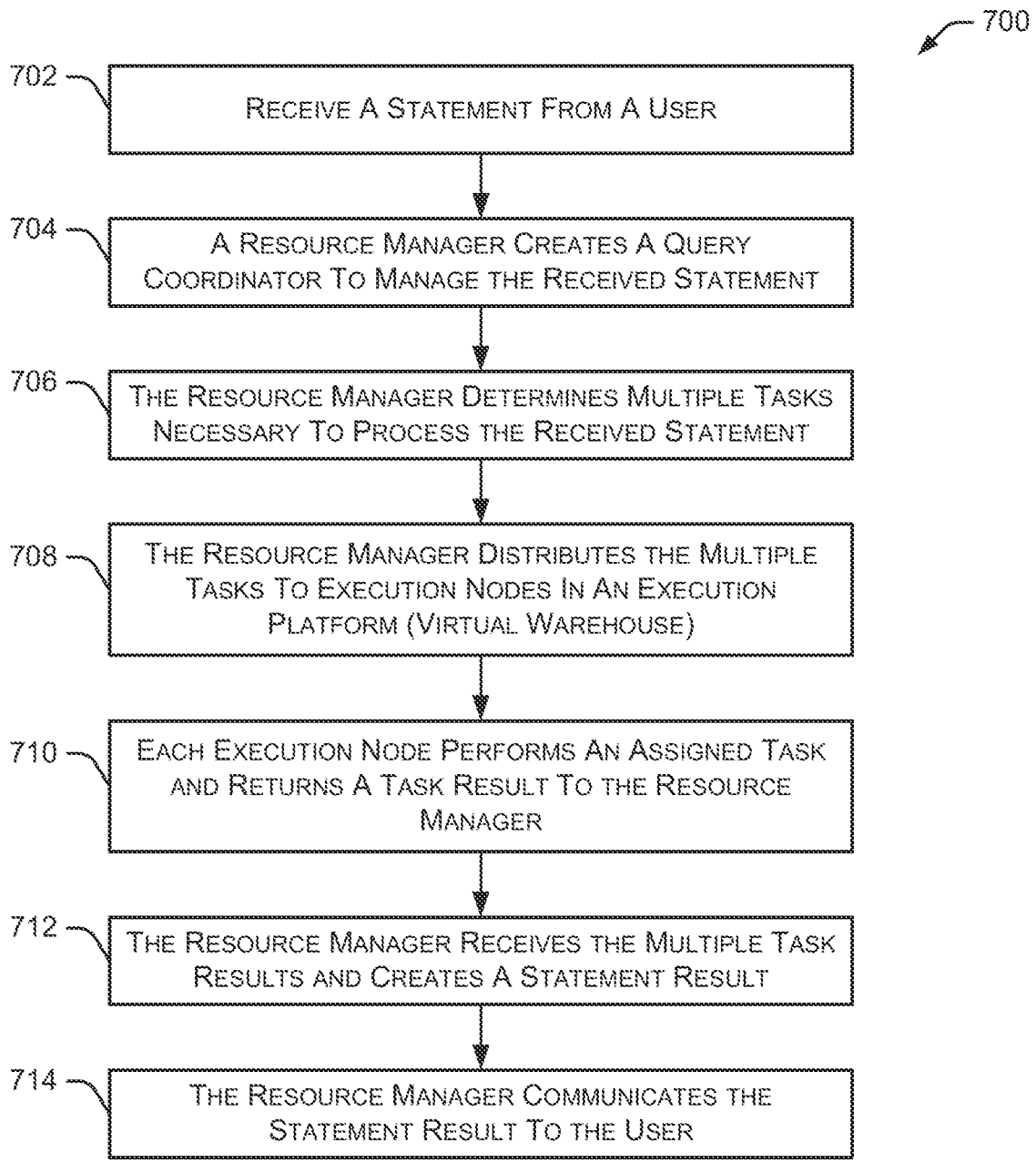
FIG. 7 is a flow diagram depicting an embodiment of a method for managing data storage and retrieval operations.

FIG. 7 is a flow diagram depicting an embodiment of a method 700 for managing data storage and retrieval operations. Initially, method 700 receives a statement, request or query from a user at 702. A statement is any request or command to perform a data-related operation. Example statements include data retrieval requests, data storage requests, data transfer requests, data queries, and the like. In some embodiments, the statement is implemented as an SQL statement. A resource manager creates a query coordinator at 704 to manage the received statement. For example, the query coordinator manages the various tasks necessary to process the received statement, including interacting with an execution platform and one or more data storage devices. In some embodiments, the query coordinator is a temporary routine created specifically to manage the received statement.

Method 700 continues as the resource manager determines multiple tasks necessary to process the received statement at 706. The multiple tasks may include, for example, accessing data from a cache in an execution node, retrieving data from a remote storage device, updating data in a cache, storing data in a remote storage device, and the like. The resource manager also distributes the multiple tasks to execution nodes in the execution platform at 708. As discussed herein, the execution nodes in the execution platform are implemented within virtual warehouses. Each execution node performs an assigned task and returns a task result to the resource manager at 710. In some embodiments, the execution nodes return the task results to the query coordinator. The resource manager receives the multiple task results and creates a statement result at 712, and communicates the statement result to the user at 714. In some embodiments, the query coordinator is deleted after the statement result is communicated to the user.

Figure 8:
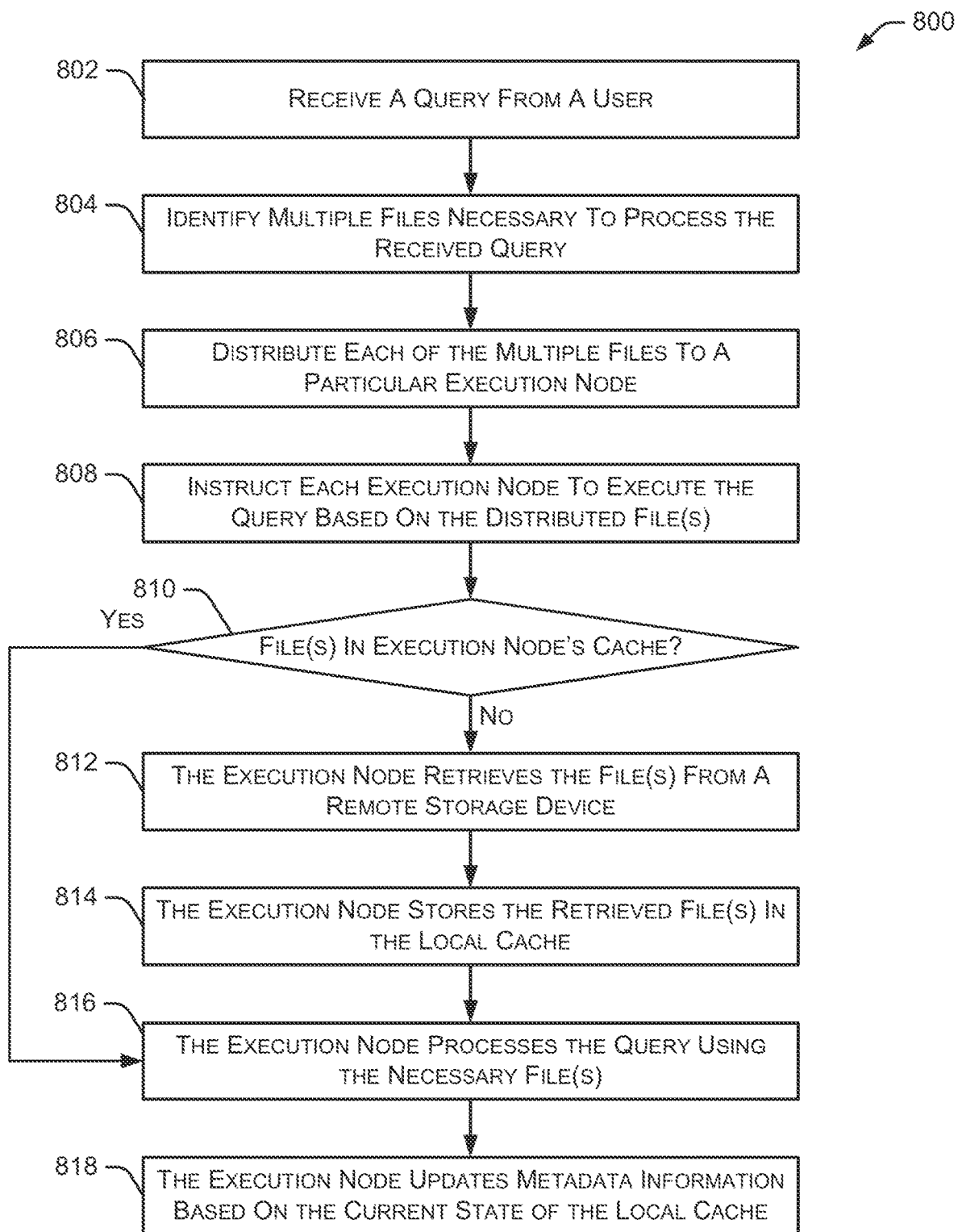
FIG. 8 is a flow diagram depicting an embodiment of a method for managing a data cache.

FIG. 8 is a flow diagram depicting an embodiment of a method 800 for managing a data cache. Initially, method 800 receives (or identifies) a query from a user at 802. Method 800 identifies multiple files necessary to process the received query at 804. To process the multiple files at substantially the same time, each of the multiple files are distributed to a particular execution node for processing at 806. In particular embodiments, any number of execution nodes are used to process the multiple files. Each of the execution nodes are instructed to execute the query at 808 based on the files distributed to that execution node.

Method 800 continues as each execution node determines at 810 whether the files distributed to the execution node are stored in the execution node's cache. The execution node's cache may also be referred to as a "local cache." If the files are already stored in the execution node's cache, the execution node processes the query using those cached files at 816. However, if one or more of the files are not stored in the execution node's cache, the execution node retrieves the non-cached files from a remote storage device at 812. The execution node stores the retrieved files in the local cache at 814, and processes the query using the retrieved files at 816. In some embodiments the execution node modifies the retrieved file prior to storing the file in the local cache. For example, the execution node may decrypt an encrypted file or decompress a compressed file. By decrypting or decompressing the file prior to caching, the execution node only performs that modification once, instead of decrypting or decompressing the file each time it is accessed from the local cache.

After processing the query, the execution node updates metadata information based on the current state of the local cache at 818. Metadata 110 (FIG. 1) stores information about data cached in each execution node. Thus, each time data in an execution node is updated (e.g., new data is cached or data is moved from a fast memory to a slower HDD), metadata 110 is updated to reflect the execution node update.

In some embodiments, the received query contains a single instruction. That single instruction is implemented by each of the multiple execution nodes at substantially the same time. Although each of the multiple execution nodes are implementing the same instruction, each execution node is responsible for different files on which the instruction is implemented. Thus, the single instruction is implemented on multiple different data files by the multiple execution nodes in parallel with one another.

The example systems and methods described herein provide a distributed cache architecture within a single virtual warehouse or across multiple virtual warehouses. Each execution node in a particular virtual warehouse has its own cache. The multiple execution nodes in the particular virtual warehouse form a distributed cache (i.e., distributed across the multiple execution nodes). In other embodiments, the cache may be distributed across multiple execution nodes contained in multiple different virtual warehouses.

In some implementations, the same file is cached by multiple execution nodes at the same time. This multiple caching of files helps with load balancing (e.g., balancing data processing tasks) across multiple execution nodes. Additionally, caching a file in multiple execution nodes helps avoid potential bottlenecks when significant amounts of data are trying to pass through the same communication link. This implementation also supports the parallel processing of the same data by different execution nodes.

The systems and methods described herein take advantage of the benefits of both shared-disk systems and the shared-nothing architecture. The described platform for storing and retrieving data is scalable like the shared-nothing architecture once data is cached locally. It also has all the benefits of a shared-disk architecture where processing nodes can be added and removed without any constraints (e.g., for 0 to N) and without requiring any explicit reshuffling of data.

In some embodiments, one or more of the caches contained in the execution nodes are multi-level caches that include different types of data storage devices. For example, a particular cache may have a hierarchy of data storage devices that provide different data access speeds. In one embodiment, a cache includes memory that provides the fastest data access speed, a solid-state drive (SSD) that provides intermediate data access speed, and a hard disk drive (HDD) that provides slower data access speed. Resource manager 102 (FIG. 1) and/or other systems can manage which data is stored in the different data storage devices. For example, the most frequently accessed data is stored in the memory and the least frequently accessed data is stored in the hard disk drive. In some embodiments, a least-recently used (LRU) algorithm is utilized to manage the storage of data in the multiple storage devices. For example, the LRU algorithm may determine whether to store particular data in a fast memory or a slower storage device. In some implementations, the LRU algorithm also determines which data to remove from a cache.

In some embodiments, only a portion of certain files are cached. For example, when data is stored in a columnar format and only certain columns within the file are being accessed on a regular basis, the system may choose to cache the columns being accessed (and not cache the other columns). This approach preserves the cache storage space and provides an effective use of the available cache resources. Additionally, this approach reduces the amount of data that is copied from the remote storage devices to the cache. Rather than copying the entire file from the remote storage devices, only the relevant columns are copied from the remote storage device into the cache. In other embodiments, the described systems and methods cache certain rows within the file that are being accessed on a regular basis.

Additionally, the described systems and methods are able to prune out a piece of data when it is not relevant to a particular query without having to first access that piece of data. For example, the systems and methods minimize the amount of data loaded from a remote storage device by pruning both horizontally (the system knows the subset of rows that need to be accessed) and vertically (only the referenced columns are loaded). This is accomplished by storing the metadata (i.e., the metadata associated with the stored data) separately from the stored data. This metadata allows the systems and methods to determine which files (and which file pieces) need to be accessed for a particular task.

In some embodiments, the systems and methods described herein can save a metadata state associated with a particular cache. For example, the metadata state information may include a list of all files (or file pieces) stored in the cache and the last time each file (or file piece) was accessed. This metadata state information is saved when an execution node or virtual warehouse is hibernated. Then, when the execution node or virtual warehouse is restored, the metadata state information is used to prime the cache, thereby restoring the cache to the same state (i.e., storing the same data files) as when the hibernation occurred. Using this approach, the cache does not need to be repopulated with data over a period of time based on assigned tasks. Instead, the cache is immediately populated with data to restore the previous state without the lag time of starting with an empty cache. This process may be referred to as "warming the cache."

The metadata discussed herein may include information regarding offsets in a file. For example, the metadata may identify all pieces of a particular file and include a map of the file (i.e., a map identifying all pieces of the file). The metadata associated with the file pieces may include a file name, a file size, a table to which the file belongs, a column size, a column location, and the like. The column location may be expressed as a column offset (e.g., an offset from the beginning of the file). The column offset specifies a particular location within the file. In some embodiments, this metadata is contained in the first few bytes of a file header. Thus, the system can determine from the file header how to access the pieces of the file (using the map of the file defined in the metadata) without having to access a metadata database (e.g., database 110 in FIG. 1).

In particular implementations, a cache may use multiple storage devices, such as memory and a local disk storage device. To maximize the cache hit rate, files (or portions of files) that have not been accessed recently are removed from the cache to provide storage space for other files (or portions of other files) that are being accessed more frequently.

Figure 9:
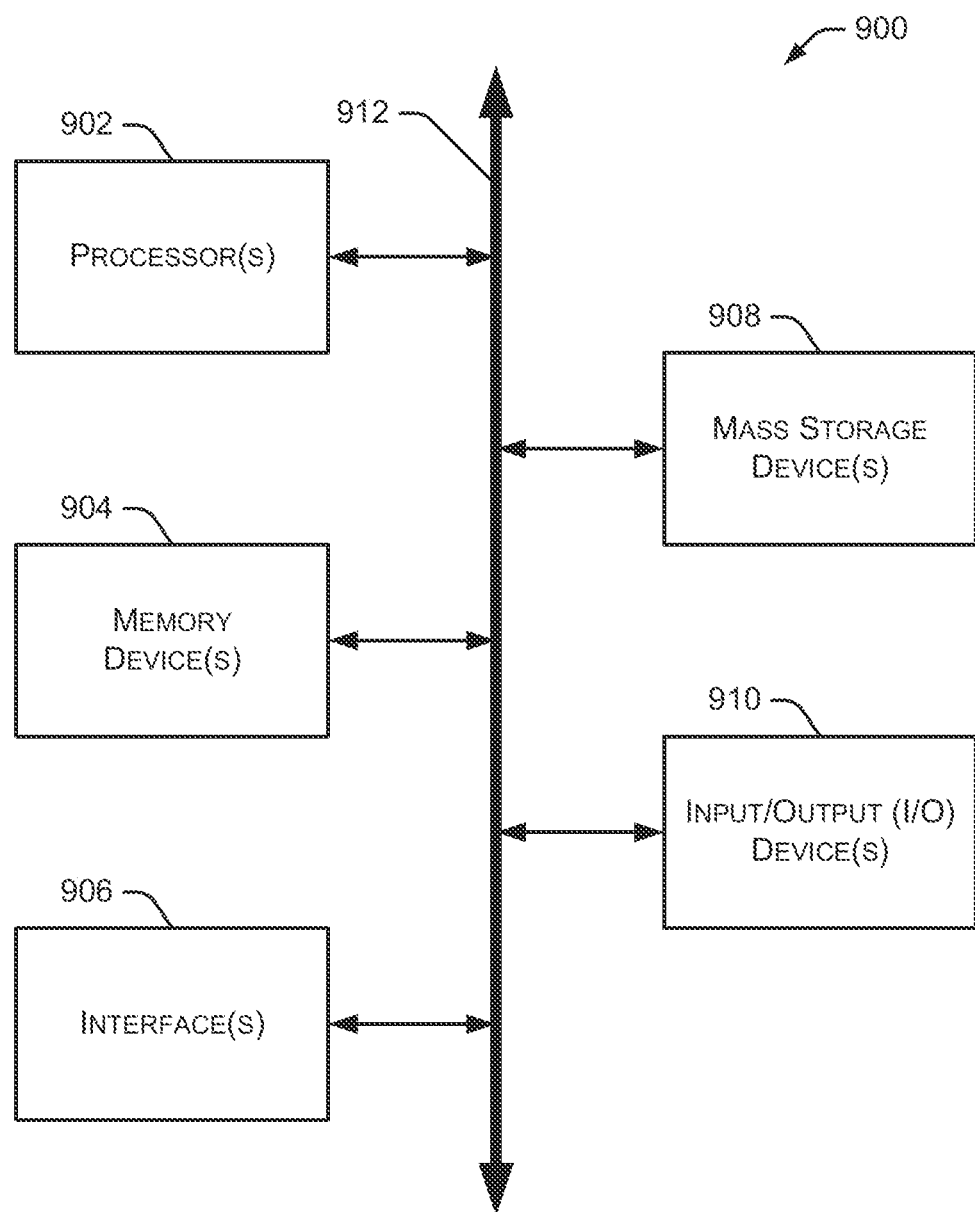
FIG. 9 is a block diagram depicting an example computing device.

FIG. 9 is a block diagram depicting an example computing device 900. In some embodiments, computing device 900 is used to implement one or more of the systems and components discussed herein. For example, computing device 900 may allow a user or administrator to access resource manager 102. Further, computing device 900 may interact with any of the systems and components described herein. Accordingly, computing device 900 may be used to perform various procedures and tasks, such as those discussed herein. Computing device 900 can function as a server, a client or any other computing entity. Computing device 900 can be any of a wide variety of computing devices, such as a desktop computer, a notebook computer, a server computer, a handheld computer, a tablet, and the like.

Computing device 900 includes one or more processor(s) 902, one or more memory device(s) 904, one or more interface(s) 906, one or more mass storage device(s) 908, and one or more Input/Output (I/O) device(s) 910, all of which are coupled to a bus 912. Processor(s) 902 include one or more processors or controllers that execute instructions stored in memory device(s) 904 and/or mass storage device(s) 908. Processor(s) 902 may also include various types of computer-readable media, such as cache memory.

Memory device(s) 904 include various computer-readable media, such as volatile memory (e.g., random access memory (RAM)) and/or nonvolatile memory (e.g., read-only memory (ROM)). Memory device(s) 904 may also include rewritable ROM, such as Flash memory.

Mass storage device(s) 908 include various computer readable media, such as magnetic tapes, magnetic disks, optical disks, solid state memory (e.g., Flash memory), and so forth. Various drives may also be included in mass storage device(s) 908 to enable reading from and/or writing to the various computer readable media. Mass storage device(s) 908 include removable media and/or non-removable media.

I/O device(s) 910 include various devices that allow data and/or other information to be input to or retrieved from computing device 900. Example I/O device(s) 910 include cursor control devices, keyboards, keypads, microphones, monitors or other display devices, speakers, printers, network interface cards, modems, lenses, CCDs or other image capture devices, and the like.

Interface(s) 906 include various interfaces that allow computing device 900 to interact with other systems, devices, or computing environments. Example interface(s) 906 include any number of different network interfaces, such as interfaces to local area networks (LANs), wide area networks (WANs), wireless networks, and the Internet.

Bus 912 allows processor(s) 902, memory device(s) 904, interface(s) 906, mass storage device(s) 908, and I/O device(s) 910 to communicate with one another, as well as other devices or components coupled to bus 912. Bus 912 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 900, and are executed by processor(s) 902. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

Although the present disclosure is described in terms of certain preferred embodiments, other embodiments will be apparent to those of ordinary skill in the art, given the benefit of this disclosure, including embodiments that do not provide all of the benefits and features set forth herein, which are also within the scope of this disclosure. It is to be understood that other embodiments may be utilized, without departing from the scope of the present disclosure.

The invention claimed is:

1. A non-transitory computer-readable medium storing instructions which, when executed by one or more second processors of a computing device, cause the one or more second processors to:
   receive a plurality of queries for information stored in one or more databases to be processed by a plurality of virtual warehouses that includes a first plurality of processors, wherein each of the plurality of virtual warehouses includes multiple ones of the first plurality of processors and corresponding local storage;
   identify a plurality of query tasks associated with the plurality of queries;
   distribute, with the one or more second processors, the plurality of query tasks to a plurality of virtual warehouses using at least a set of statistics associated with the first plurality of processors, wherein the set of statistics is accumulated from at least one of the previously executed query tasks by at least one of the first plurality of processors, the set of statistics is stored separately from a local storage of each of the first plurality of processors and each of first plurality of processors is stateless with respect to the set of statistics;
   change, during the processing of the plurality of the query tasks by the plurality of virtual warehouses, a total number of virtual warehouses in the plurality of virtual warehouses is using a load of the plurality of virtual warehouses due to the processing of the plurality of query tasks by the plurality of virtual warehouses, wherein the change is at least one of creating a new virtual warehouse or deleting an existing virtual warehouse and the change in the total number of virtual warehouses are made in a unit of the multiple ones of the first plurality of processors and the corresponding local storage, wherein cache resources associated with the new virtual warehouse are populated with one or more data files associated with the processing of the plurality of query tasks at the time the virtual warehouse is created and wherein the cache resources vary among the plurality of processors, wherein a first subset of the plurality of processors comprises minimal cache resources and a second subset of the plurality of processors comprises cache resources providing faster input-output operations;

execute the plurality of query tasks with the first plurality of processors;

as a result of the change in the total number of virtual warehouses, redistribute the one or more query tasks of the plurality of query tasks to the plurality of virtual warehouses, the one or more query tasks to be executed by the one or more associated processors of a second plurality of processors; and in response to executing the plurality of query tasks, update at least a portion of the set of statistics based on at least one of the executed query tasks with the plurality of processors.

2. The non-transitory machine-readable medium of claim 1, wherein the executing of the plurality of query tasks uses at least a plurality of database tables.

3. The non-transitory machine-readable medium of claim 2, wherein at least some of the plurality of database tables are encrypted and are subsequently decrypted before the executing of the plurality of query tasks.

4. The non-transitory machine-readable medium of claim 2, wherein at least some of the plurality of database tables are compressed and are subsequently decompressed before the executing of the plurality of query tasks.

5. The non-transitory machine-readable medium of claim 2, wherein each of the first plurality of processors processes a corresponding one of the plurality of database tables, and wherein data from the plurality of database tables is stored in a cache associated with that processor.

6. The non-transitory machine-readable medium of claim 1, wherein the query is received from a client, and wherein the instructions further cause the one or more second processors to:

generate a result from the execution of the plurality of query tasks, and data from the result to the client associated with the query.

7. The non-transitory machine-readable medium of claim 1, wherein the instructions further cause the computing device to:

optimize the plurality of queries.

8. The non-transitory computer-readable medium of claim 1, wherein the set of data is stored in a relational database.

9. The non-transitory computer-readable medium of claim 8, wherein the relational database is a structured query language database.

10. The non-transitory computer-readable medium of claim 1, wherein the database system is a multi-tenant database that isolates computing resources and data between different customers.

11. The non-transitory computer-readable medium of claim 1, wherein at least one of the databases is external to a system that includes the first plurality of processors.

12. The non-transitory computer-readable medium of claim 1, wherein the statistics comprise metadata related to the one or more databases.

13. The non-transitory computer-readable medium of claim 1, wherein the accumulation of the set of statistics from the at least one of the previously executed query tasks occurs automatically.

14. The non-transitory computer-readable medium of claim 1, wherein the updating of the at least the portion of the set of statistics occurs automatically.

15. A method comprising:

receiving a plurality of queries with a database system to be processed by a plurality of virtual warehouses that includes a first plurality of processors, wherein each of the plurality of virtual warehouses includes multiple ones of the first plurality of processors and corresponding local storage;

identifying a plurality of query tasks associated with the plurality of queries;

distributing, with the one or more second processors, the plurality of query tasks to a plurality of virtual warehouses using at least a set of statistics associated with the first plurality of processors, wherein the set of statistics is accumulated from at least one of the previously executed query tasks by at least one of the first plurality of processors, the set of statistics is stored separately from a local storage of each of the first plurality of processors and each of first plurality of processors is stateless with respect to the set of statistics;

changing, during the processing of the plurality of the query tasks by the plurality of virtual warehouses, a total number of virtual warehouses in the plurality of virtual warehouses is using a load of the plurality of virtual warehouses due to the processing of the plurality of query tasks by the plurality of virtual warehouses, wherein the change is creating a new virtual warehouse and the change in the total number of virtual warehouses are made in a unit of the multiple ones of the first plurality of processors and the corresponding local storage, wherein cache resources associated with the new virtual warehouse are populated with data files associated with the processing of the plurality of query tasks at the time the virtual warehouse is created, based at least in part on the expected tasks to be performed by the new virtual warehouse and wherein the cache resources vary among the plurality of processors, wherein a first subset of the plurality of processors comprises minimal cache resources and a second subset of the plurality of processors comprises cache resources providing faster input-output operations;

executing the plurality of query tasks with the first plurality of processors;

as a result of the change in the total number of virtual warehouses, redistributing the one or more query tasks of the plurality of query tasks to the plurality of virtual warehouses, the one or more query tasks to be executed by the one or more associated processors of a second plurality of processors; and in response to executing the plurality of query tasks, updating at least a portion of the set of statistics based on at least one of the executed query tasks with the first plurality of processors.

16. The method of claim 15, wherein the executing of the plurality of query tasks uses at least a plurality of database tables.

17. The method of claim 16, wherein at least some of the plurality of database tables are encrypted and are subsequently decrypted before the executing of the plurality of query tasks.

18. The method of claim 16, wherein at least some of the plurality of database tables are compressed and are subsequently decompressed before the executing of the plurality of query tasks.

19. The method of claim 16, wherein each of the first plurality of processors processes a corresponding one of the plurality of database tables, and wherein data from the plurality of database tables is stored in a cache associated with those processors.

20. The method of claim 15, wherein the query is received from a client, and further comprising:
returning a result to a query coordinator.

21. The method of claim 15, further comprising:
optimizing the plurality of queries.

22. The method of claim 15, wherein the set of data is stored in a relational database.

23. The method of claim 15, wherein the relational database is a structured query language database.

24. The method of claim 15, wherein the database system is a multi-tenant database that isolates computing resources and data between different customers.

25. The method of claim 15, wherein at least one of the databases is external to a system that includes the first plurality of processors.

26. The method of claim 15, wherein the statistics comprise metadata related to the one or more databases.

27. The method of claim 15, wherein the accumulation of the set of statistics from the at least one of the previously executed query tasks occurs automatically.

28. The method of claim 15, wherein the updating of the at least the portion of the set of statistics occurs automatically.

29. A system comprising:
one or more first processors programmed to execute a query coordinator process, the query coordinator process to:
receive a plurality of queries for information stored in one or more databases to be processed by a plurality of virtual warehouses that includes a first plurality of processors, wherein each of the plurality of virtual warehouses includes multiple ones of the first plurality of processors and corresponding local storage,
identify a plurality of query tasks associated with the plurality of queries,
distribute the plurality of query tasks to a plurality of virtual warehouses using at least a set of statistics associated with the first plurality of processors, wherein the set of statistics is accumulated from at least one of the previously executed query tasks by at least one of the first plurality of processors, the set of statistics is stored separately from a local storage of each of the first plurality of processors and each of first plurality of processors is stateless with respect to the set of statistics, and
change, during the processing of the plurality of the query tasks by the plurality of virtual warehouses, a total number of virtual warehouses in the plurality of virtual warehouses is using a load of the plurality of virtual warehouses due to the processing of the plurality of query tasks by the plurality of virtual warehouses, wherein the change is at least one of creating a new virtual warehouse or deleting an existing virtual warehouse and the change in the total number of virtual warehouses are made in a unit of the multiple ones of the first plurality of processors and the corresponding local storage, wherein cache resources associated with the new virtual warehouse are populated with data files associated with the processing of the plurality of query tasks at the time the virtual warehouse is created, based at least in part on the expected tasks to be performed by the new virtual warehouse and wherein the cache resources vary among the plurality of processors, wherein a first subset of the plurality of processors comprises minimal cache resources and a second subset of the plurality of processors comprises cache resources providing faster input-output operations; and
the plurality of second processors programmed to:
execute the plurality of query tasks, wherein the query coordinator process is further programmed to, in response to executing the plurality of query tasks, update at least a portion of the set of statistics based on at least one of the executed query tasks with the plurality of processors; and
as a result of the change in the total number of virtual warehouses, redistribute the one or more query tasks of the plurality of query tasks to the plurality of virtual warehouses, the one or more query tasks to be executed by the one or more associated processors of a second plurality of processors.

30. The system of claim 29, wherein the executing of the plurality of query tasks uses at least a plurality of database tables.

* * * * *